United States Patent
Uematsu

[19]

[11] Patent Number: 6,143,515
[45] Date of Patent: Nov. 7, 2000

[54] PROCESS FOR EVALUATING MICROBIAL-DEGRADABILITY OF ORGANIC MATTERS AND APPARATUS THEREFOR

[75] Inventor: Shogo Uematsu, Shizuoka, Japan

[73] Assignee: Saida Ironworks Co., Ltd., Yaizu, Japan

[21] Appl. No.: 09/166,724

[22] Filed: Oct. 5, 1998

[30] Foreign Application Priority Data

Oct. 9, 1997 [JP] Japan ................................. 9-293597

[51] Int. Cl.$^7$ .............................. C12Q 1/02; C12M 1/00; C12M 1/36
[52] U.S. Cl. ..................... 435/29; 435/283.1; 435/286.1; 435/286.6; 435/287.5; 435/289.1; 435/290.1; 435/290.4
[58] Field of Search ............................... 435/29, 4, 283.1, 435/286.1, 286.6, 287.5, 289.1, 290.1, 290.4

[56] References Cited

U.S. PATENT DOCUMENTS

| | | | |
|---|---|---|---|
| 5,466,273 | 11/1995 | Connell | 71/11 |
| 5,580,770 | 12/1996 | DeFillippi | 435/180 |
| 5,648,264 | 7/1997 | Kume | 435/264 |
| 5,738,703 | 4/1998 | Bandurski | 71/9 |
| 5,772,721 | 6/1998 | Kazemzadeh | 71/11 |

OTHER PUBLICATIONS

Biodegradable Polymers and Plastics: Microstructure and Biodegradability of mater–BI Products by C. Bastioloi et al. pp. 101–111 (1993).

American Society for Testing and Materials Designation D 5209–92. "Standard Test Method for Determining the Aerobic Biodegradation of Plastic Materials in the Presence of Municipal Sewage Sludge", p. 1–4 (1992).

American Society for Testing and Materials Designation D 5338–92. "Standard Test Method for Determining the Aerobic Biodegradation of Plastic Materials Under Controlled Composting Conditions" p. 1–16.

Primary Examiner—Louise N. Leary
Attorney, Agent, or Firm—Jordan and Hamburg LLP

[57] ABSTRACT

The disclosed in an invention directed to carrying out accurate and easy evaluation of microbial-degradability of organic matters objectively. To carry out a method for evaluating microbial-degradability of an organic matter, an organic matter as an evaluation subject is placed together with a certain prescribed microbial source into a reaction column maintained constantly at a fixed temperature to effect decomposition of the organic matter by microorganisms contained in the prescribed microbial source under feeding of $CO_2$-free saturated water vapor into the reaction column and to measure the weight of carbon dioxide formed by the decomposition. A cellulose as a evaluation reference is also decomposed likewise to measure the weight of carbon dioxide formed by the decomposition, and then comparative discussion of these two measured values is carried out so as to evaluate degradability of the organic matter.

12 Claims, 6 Drawing Sheets

PROCESS FOR EVALUATING MICROBIAL-DEGRADABILITY OF ORGANIC MATTERS AND APPARATUS THEREFOR

BACKGROUND OF THE INVENTION

1. Field of the Invention

The present invention relates to a process for evaluating microbial-degradability of organic matters and an apparatus employed therefor, particularly to a process and an apparatus for evaluating microbial-degradability of biodegradable plastics, organic industrial waste including hardly degradable organic matters such as PCB and other organic matters.

2. Earlier Technologies

Environmental disruption brought about by industrial waste is now of a global concern. That is, pollution of soil and pollution of ocean to be caused by damping industrial waste into the soil or at the sea can be causative of disruption of ecosystem including the human society, giving rise to a serious social problem. Under such circumstances, degradation of organic waste to be achieved by microorganisms is the cleanest purification system that occurs in the realm of nature. Accordingly, to substitute those substances which are now chemically synthesized with those having microbial-degradability can be a useful measure for solving or improving the problem of environmental disruption induced by industrial waste as described above.

As an example of such substance having microbial degradability, biodegradable plastics which are decomposed by soil or water microorganisms are under development and are sharing some part of organic industrial waste. The biodegradable plastics are expected:

(1) to be stable during the period of use, and (2) to be decomposed soon in the soil by microorganisms after disposal.

Although it is possible to measure the period during which biodegradable plastics can be used stably, there is established no standardized means of measuring the rate of degradation in biodegradable plastics to be caused by microorganisms, so that evaluation results of biodegradable plastics are of inconsistency, which is a main cause of hindering development of high-quality biodegradable plastics.

There exists so far no evaluation apparatus relating to total degradation of organic matters in the soil and in compost into carbon dioxide (carbonic acid gas). As carbon dioxide analytical methods, the following methods are generally known:

(1) quantitative determination of carbon dioxide captured in a strong alkaline solution by means of neutralization titration; and (2) quantitative determination of carbon dioxide captured in a gas reservoir by use of a gas analyzer.

However, since the volume or weight of the organic matter to be tested ranges widely from 1 cc to several hundreds of tons, and besides organic matters are of different compositions, there is reported no standardized test method. Accordingly, the test method (1) or (2) is selected depending on the respective subjects to be tested, with no established standardized means for evaluating biodegradability.

(a) a method in which biodegradable plastic samples are buried in various kinds of soils to allow them to be decomposed by soil microorganisms for a predetermined period. After this period, the biodegradable plastics are dug out of the soils, and their states are compared with those before they were buried; and (b) a method in which biodegradable plastics are allowed to be decomposed by activated sewage sludge microorganisms to measure the amount of carbon dioxide formed by decomposition by means of titration. This method is stipulated under ASTM (American Society for Testing and Materials D5209-92, D5338-92).

However, the conventional methods for evaluating biodegradability of biodegradable plastics involve the following problems respectively.

Method (a)

This method includes indeterminate factors: variation in the kinds and numbers of inhabitant microorganisms depending on the soil in which biodegradable plastics are buried and variation in the natural conditions including temperature, rains, etc. In other words, the conditions under which the samples are decomposed by microorganisms vary greatly depending on the soil. Accordingly, evaluation of biodegradability in biodegradable plastics carried out for various kinds of soils brings about inconsistent results. That is, evaluation of biodegradability obtained according to the method (a) is of low reliability.

Method (b)

This method requires a long-term maintenance of instruments and devices and an experienced technician, because the amount of carbon dioxide formed during decomposition is adapted to be determined by titration. Further, while this method employs activated sewage water sludge from a municipal waste water treatment tank as a microbial source, it involves a problem in that the rate of decomposition to be achieved by microorganisms varies depending on the sludge employed, since the kinds and numbers of inhabitant microorganisms which achieve decomposition of biodegradable plastics vary depending on the soil employed. In other words, the measured values of biodegradability evaluation include significant errors due to the indeterminate factors in that the kinds and numbers of inhabitant microorganisms which achieve decomposition of biodegradable plastics vary depending on the sludge employed.

SUMMARY OF THE INVENTION

The present invention was accomplished with a view to solving the problems as described above and providing an easy and reliable method and apparatus for evaluating microbial-degradability of biodegradable plastics, organic industrial wastes including PCB which is a hardly-decomposable organic matter, as well as, other organic matters.

In order to solve the problems described above, the present invention provides the following method and apparatus.

An invention according to claim 1 is directed to a method for evaluating microbial-degradability of an organic matter, the method comprising:

taking an organic matter as an evaluation subject together with a prescribed microbial source into a reaction column maintained constantly at a fixed temperature to effect decomposition of the organic matter in the reaction column by microorganisms contained in the prescribed microbial source under feeding of $CO_2$-free saturated water vapor into the reaction column and to measure the weight of carbon dioxide formed by the decomposition;

taking a cellulose as a evaluation reference together with the same prescribed microbial source as described above into another reaction column maintained constantly at the same fixed temperature as described above to effect decomposition of the cellulose in the reaction column by the microorganisms contained in the prescribed microbial source under feeding of $CO_2$-free saturated water vapor into the reaction column and to measure the weight of carbon dioxide formed by the decomposition; and carrying out comparative discussion of these two measured values so as to evaluate degradability of the organic matter.

According to the invention as defined in claim 1, an organic matter as a subject to be tested and a cellulose which is most preferred as an evaluation reference are allowed to be decomposed respectively under the same conditions by microorganisms using the same prescribed microbial source, to make comparative discussion of degradability of the former and that of the latter and evaluate degradability of the test subject organic matter.

The inside of the reaction column is maintained constantly at a fixed temperature, and the test subject organic matter or the evaluation reference cellulose is contained in the reaction column together with the prescribed microbial source, so that the organic matter and the cellulose are decomposed by the microorganisms under the same conditions. Since the saturated water vapor to be supplied to each reaction column contains no carbon dioxide, it does not interfere with the measurement of the weight of carbon dioxide formed by the decomposition of the organic matter or of the cellulose. The microorganisms decompose the organic matter or the cellulose in the presence of the saturated water vapor fed into the reaction column. The microbial-degradability of the organic matter can be evaluated by carrying out comparative discussion of the measured value in terms of the weight of carbon dioxide formed by decomposition of the organic matter and the measured value in terms of the weight of carbon dioxide formed by decomposition of the cellulose.

In an invention as defined in claim 2, a mixture of a compost having a predetermined formulation and sea sand is used as the prescribed microbial source.

According to the invention as defined in claim 2, since a mixture of a compost having a predetermined formulation and sea sand is used as the prescribed microbial source, the microbial source is always constant.

According to inventions as defined in claims 3 and 4, the weight of carbon dioxide formed by the decomposition of the organic matter and the weight of carbon dioxide formed by the decomposition of the cellulose are determined by allowing each carbon dioxide to be adsorbed by soda lime and measuring the weight gain in the soda lime.

According to inventions as defined in claims 3 and 4, since the weight of carbon dioxide formed by the decomposition of the organic matter and the weight of carbon dioxide formed by the decomposition of the cellulose are determined respectively by allowing each carbon dioxide to be adsorbed by soda lime and measuring the weight gain in the soda lime, this method requires extremely easy measurement procedures, and even inexperienced operators can carry out easy measurement.

The apparatuses set forth in claims 5 to 12 are directed to carry out the methods of claims 1 to 3, and they exhibit the effects described referring to the methods of claims 1 to 3.

An apparatus according to an invention as defined in claim 5 is designed for evaluating microbial-degradability of an organic matter, the apparatus comprising: a reaction column maintained constantly at a fixed temperature and containing an organic matter as an evaluation subject or a cellulose as an evaluation reference together with a prescribed microbial source; means for forming saturated water vapor, connected to one end of the reaction column, the means being provided with first $CO_2$ adsorption means and feeding $CO_2$-free saturated water vapor into the reaction column; and an adsorption column, connected to the other end of the reaction column, the adsorption column containing second carbon dioxide adsorption means.

According to the invention as defined in claim 5, since means for forming saturated water vapor is provided with the first $CO_2$ adsorption means, the saturated water vapor formed thereby contains no carbon dioxide. The $CO_2$-free saturated water vapor is fed into the reaction column to effect decomposition of the organic matter as an evaluation subject or the cellulose as an evaluation reference. Since the inside of the reaction column is maintained constantly at a fixed temperature and an organic matter as an evaluation subject or a cellulose as an evaluation reference is contained in the reaction column together with a prescribed microbial source, microbial-decomposition of the organic matter and that of the cellulose are decomposed under the same conditions. Since the saturated water vapor to be fed into the reaction column contains no carbon dioxide, it does not interfere with the measurement of carbon dioxide formed by decomposition of the organic matter or of the cellulose. The carbon dioxide formed by the decomposition of the organic matter or of the cellulose is adsorbed by the second $CO_2$ adsorption means contained in the adsorption column connected to the other end of the reaction column. The amount of carbon dioxide can be determined by measuring the weight gain in the adsorption means having adsorbed carbon dioxide. As described above, it is extremely easy to determine the weight of carbon dioxide by measuring the weigh gain in the adsorption means caused by adsorption of carbon dioxide, and even inexperienced operators can carry out easy measurement.

Further, these apparatuses are of so simple structures that they can be offered inexpensively and also can be used stably over extended periods.

In an apparatus according to an invention as defined in claim 6, a mixture of a compost having a predetermined formulation and sea sand is used as the prescribed microbial source.

According to the invention as defined in claim 6, since a mixture of a compost having a predetermined formulation and sea sand is used as the prescribed microbial source, the microbial source is always the same.

In an apparatus according to inventions as defined in claims 7 and 8, the first and second carbon dioxide adsorption means each are soda lime.

According to the inventions as defined in claims 7 and 8, soda lime constituting the first and second carbon dioxide adsorption means favorably carries out adsorption of carbon dioxide.

In an apparatus according to inventions as defined in claims 9 to 12, the adsorption column is connected to the other end of the reaction column via a water-removing column or a desiccation column.

According to the inventions as defined in claims 9 to 12, while the carbon dioxide formed by the decomposition of the organic matter or of the cellulose is fed out of the reaction column together with the saturated water vapor, the water content of the saturated water vapor is removed by the water-removing column or the desiccation column. The resulting dry air obtained by dehydration and carbon dioxide are fed into the adsorption column where the carbon dioxide is adsorbed.

The invention is not particularly limited to the above description, but the above and other objects, features, and advantages of the invention will become more apparent from the following detailed description taken in conjunction with the accompanying drawings. It is to be understood that various changes and modification may be made thereto without departing from the spirit and scope thereof.

DETAILED DESCRIPTION OF THE PREFERRED EMBODIMENTS

Preferred embodiments of the present invention will now be described with reference to the accompanied drawings.

Next, embodiments of the present invention will be described referring to the attached drawings.

First, the method according to the present invention will be described.

Figure 1:
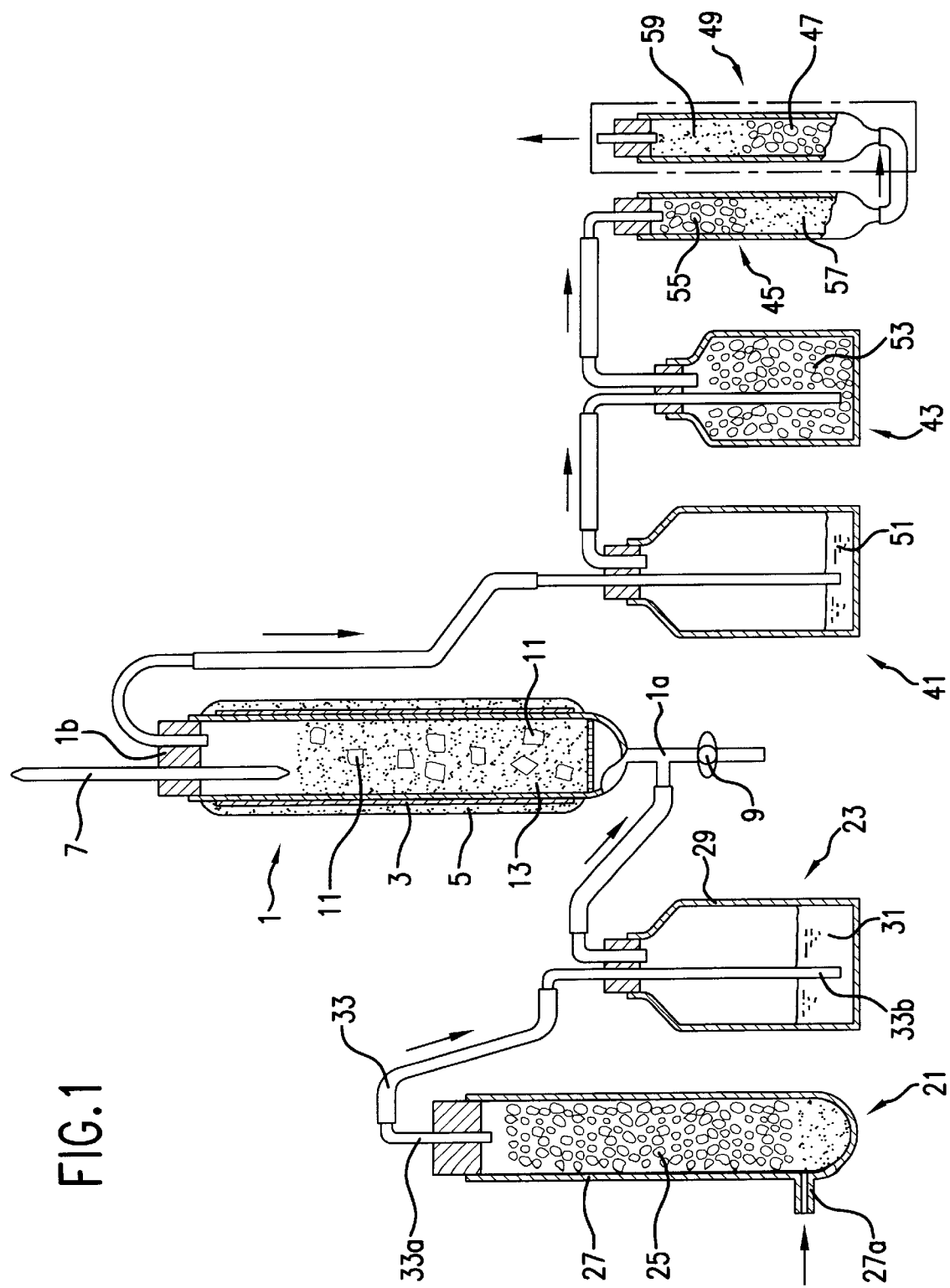
FIG. 1 is an explanatory view showing an embodiment of the apparatus for evaluating microbial-degradability of organic matters.
Figure 2:
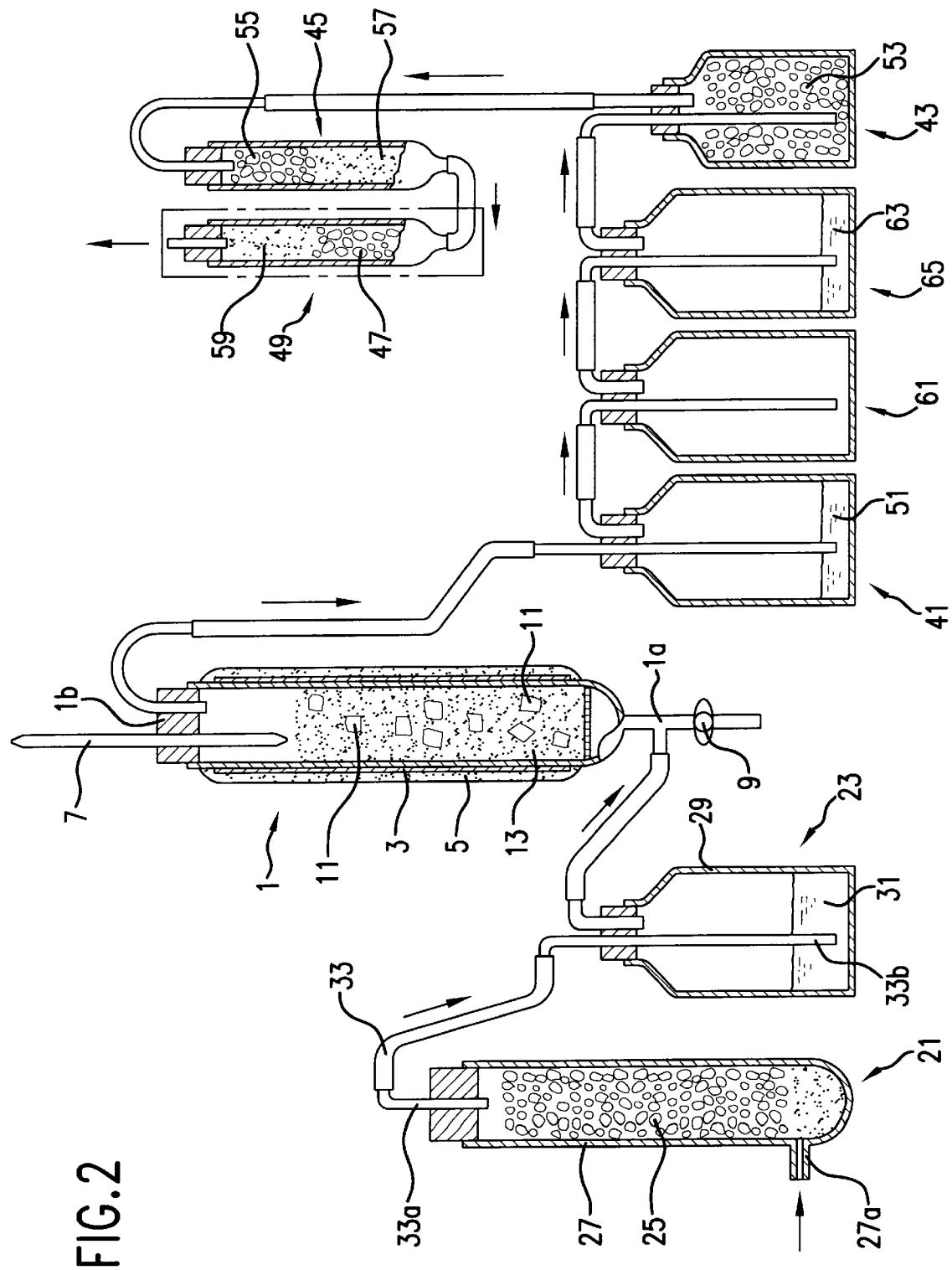
FIG. 2 is an explanatory view showing another embodiment of the apparatus for evaluating microbial-degradability of organic matters.

The numeral 1 denotes a reaction column. The inside of the reaction column 1 is maintained constantly at a fixed temperature. More specifically, for example, as shown in FIG. 1 or 2, an electric heater 3 is disposed to surround the reaction column 1, and a heat insulating material 5 is disposed to surround and allow the electric heater 3 to control the internal temperature of the reaction column 1. The numerals 7 and 9 denote a thermometer and a drain cock, respectively.

An organic matter 11 is introduced as an evaluation subject into the reaction column 1 together with a prescribed microbial source 13. As the prescribed microbial source 13, a mixture of compost having a predetermined formulation and sea sand is preferably used. To describe an example, a mixture of rinsed sea sand and aged farmyard compost made from sawdust and poultry manure is used as the prescribed microbial source 13.

A $CO_2$-free saturated water vapor is fed into the reaction column 1 to allow the microorganisms contained in the prescribed microbial source 13 to decompose the organic matter 11 in the reaction column 1, and the weight of carbon dioxide formed by the decomposition is measured to evaluate degradability of the organic matter 11.

In the measurement of the weight of carbon dioxide formed by the decomposition of the organic matter 11, carbon dioxide is adsorbed preferably by soda lime to measure the weight gain in the soda lime having adsorbed carbon dioxide, and this measured value of weight gain shall be regarded as the weight of carbon dioxide.

Meanwhile, a cellulose is introduced as the evaluation reference into another reaction column 1 maintained constantly at the same fixed temperature as described above together with the same prescribed microbial source 13 as described above, and $CO_2$-free saturated water vapor is likewise introduced thereto to allow the microorganisms contained in the prescribed microbial source 13 to decompose the cellulose in the reaction column 1, and the weight of carbon dioxide formed by the decomposition of the cellulose to carry out comparative discussion of these two measured values obtained and evaluate degradability of the organic matter 11.

Next, the apparatus for carrying out the above method will be described referring to FIG. 1.

The reaction column 1 is connected at one end (upstream end) 1a to saturated water vapor forming means 23 provided with first $CO_2$ adsorption means 21 so that $CO_2$-free saturated water vapor can be fed by this means 23 into the reaction column 1. The first $CO_2$ adsorption means 21 is, for example, soda lime 25 which is contained in an adsorption column 27. The saturated water vapor forming means 23 consists of a vapor formation column 29 and water 31 contained therein. A connecting pipe 33 is attached at one end 33a to the adsorption column 27 in the first $CO_2$ adsorption means 21, with the other end 33b opening into the water 31 contained in the vapor formation column 29. Air is introduced through an inlet port 27a into the adsorption column 27 in the first $CO_2$ adsorption means 21. This air feeding is carried out preferably at a rate of 30 ml/min so as to avoid anaerobic fermentation in the reaction column 1.

The reaction column 1 is connected at the other end (downstream end) 1b via a water-removing column 41 and a desiccation columns 43 and 45 to an adsorption column 49 containing second $CO_2$ adsorption means 47. The second $CO_2$ adsorption means 47 is preferably soda lime. The water-removing column 41 contains $2N—H_2SO_4$ (numeral 51), while the desiccation column 43 contains silica gel 53, and the desiccation column 45 contains silica gel and calcium chloride. The adsorption column 49 contains calcium chloride 59 in addition to soda lime as the second adsorption means 47.

The organic matter 11 is decomposed by the microorganisms in the compost to form carbon dioxide (carbonic acid gas) and ammonia gas. The carbon dioxide (carbonic acid gas) and the ammonia gas are exhausted from the reaction column 1 together with the saturated water vapor fed thereto. The ammonia gas is adsorbed by $2N—H_2SO_4$ (numeral 51) in the water-removing column 41; whereas the saturated water vapor is removed by the silica gel 53 in the desiccation column 43 and by the silica gel 55 and calcium chloride 57 in the desiccation column 45. The gas having been subjected to deammonification and dehydration as described above is then fed to the adsorption column 49 where carbon dioxide contained in the gas is captured by the soda lime as the second adsorption means 47 in the adsorption column 49. The weight of carbon dioxide formed is measured by weighing the weight gain in the adsorption column 49. A balance having a sensitivity of 10 mg or less is used for the weighing.

The apparatus shown in FIG. 2, which is a variation of the apparatus shown in FIG. 1, is designed to test biodegradability of a trace organic matter using an isotope. The apparatus shown in FIG. 2 is identical to that shown in FIG. 1, except that an empty intermediate column 61 and a water-removing column 65 containing $1N—NaOH$ (numeral 63) are interposed between the water-removing column 41 and the desiccation column 43 in the apparatus shown in FIG. 1. The $^{14}CO_2$ formed by microbial-degradation and other $CO_2$ are captured in the 1N—NaOH-containing desiccation column 65 to determine carbon dioxide in terms of $BaCO_3$. The $^{14}C$—$BaCO_3$ is determined by a liquid scintillation counter to obtain the amount of the decomposed organic matter.

Incidentally, when the amount of carbon dioxide formed is to be measured under anaerobic fermentation conditions, the measurement can be carried out in the same manner as described above through steps: feeding nitrogen gas from a nitrogen cylinder under flow rate control by a flow meter; and incorporating desulfurization. As a substance for achieving delsulfurization, a 5% $CuSO_4$ (copper sulfate) solution or a metal oxide compound such as $Ag_2O$ (silver oxide) can be employed.

EXAMPLES

Example 1
Cellulose Biodegradation Test

Rinsed sea sand, compost and cellulose according to the formulation shown in Table 1 were taken to a 5-liter plastic vessel. Then the resulting mixture was stirred well, and consequently introduced to the reaction column 1 in the apparatus shown in FIG. 1 to measure the amount of carbonic acid gas formed under the following conditions:

quantity of air flow: 30 ml/min reaction temperature: 35° C.

Figure 3:
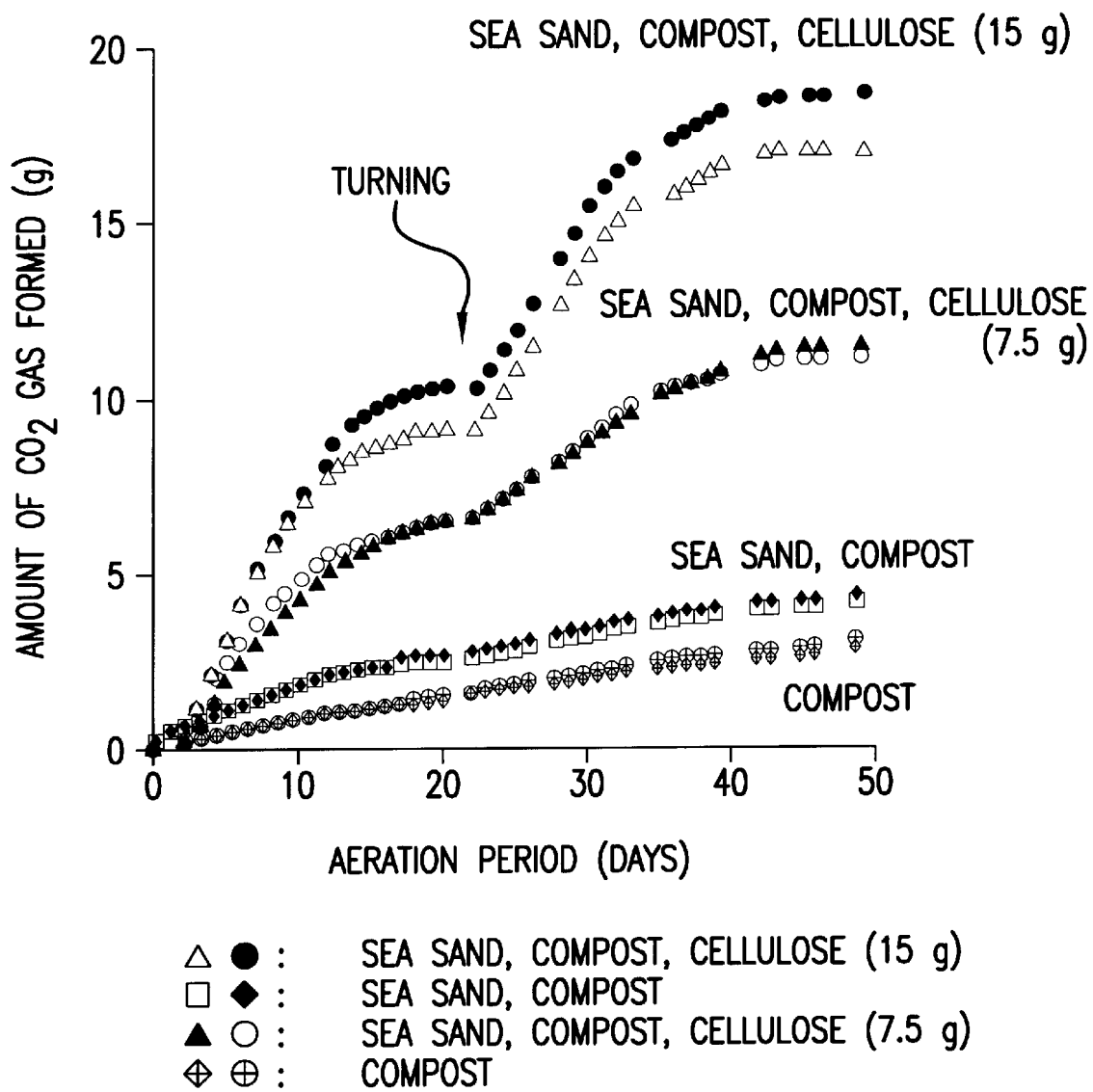
FIG. 3 is a view showing a measurement result of accumulated value of carbonic acid gas generated in Embodiment 1.

As the sea sand (grain size: 20 to 35 mesh), 250 ml of Wako's reagent grade sand was rinsed three times with distilled water, and the resulting sand from which excess of water was decanted off was used. An aged farmyard compost made from sawdust and poultry manure was subjected to selection using a 6.5-mesh official sieve, and the 6.5-mesh under fractions were used as such. As the cellulose, a filter paper powder (40 mesh) manufactured by K.K. Toyo Seisakusho was used. This cellulose was rinsed three times with distilled water, and the thus treated cellulose from which the excess of water was decanted off was used. Measurement of carbonic acid gas was carried out for 48 days, and the sample in the reaction cylinder 1 was subjected to turning on the 21st day of the reaction. The turning was carried out by transferring the sample in the reaction column 1 into a 5-liter plastic vessel and stirring it well therein. After completion of turning, the sample was returned into the reaction column 1. The results of measurement of accumulated amount of carbonic acid gas formed are shown in FIG. 3.

TABLE 1

| | | Ratio of components | | |
|---|---|---|---|---|
| Test No. | Standard | Sea sand | Compost | Cellulose |
| 1 | C | 0 ml | 500 ml | 0 g |
| 2 | 2 | 250 ml | 250 ml | 7.5 g |
| 3 | 1 | 250 ml | 250 ml | 0 g |
| 4 | 3 | 250 ml | 250 ml | 15 g |
| 5 | 1 | 250 ml | 250 ml | 0 g |
| 6 | 2 | 250 ml | 250 ml | 7.5 g |
| 7 | C | 0 ml | 500 ml | 0 g |
| 8 | 3 | 250 ml | 250 ml | 15 g |

Example 2
Test for Examining the Influence of PCB on Composting

Figure 4:
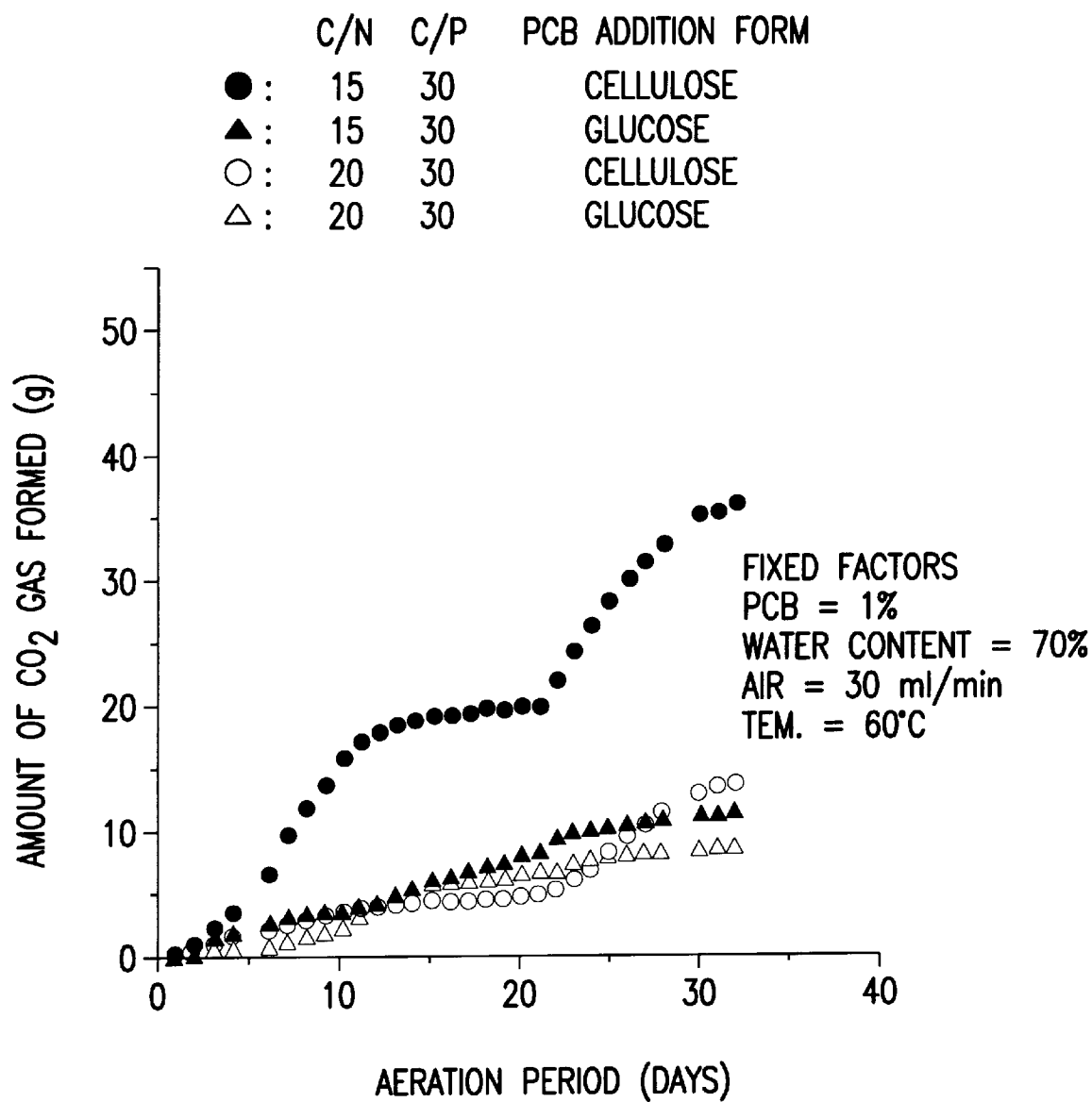
FIG. 4 is a view showing a measurement result of accumulated value of carbonic acid gas generated in Embodiment 2.

Test example for examining the influence of refractory organics PCB on composting will be shown below. To a compost raw material prepared from sawdust, poultry manure, and superphosphate, PCB was added to test the influence of PCB in the process of composting. There was used PCB (1 g) deposited on the surface of a cellulose (21 g) and on that of glucose (21 g) such that the amount of PCB may be 1% in terms of dry weight respectively. The sample was taken into a 5-liter plastic vessel and was stirred well therein in the same manner as in Example 1, and the thus treated sample was introduced into the reaction column 1 in the apparatus shown in FIG. 1. The carbon/nitrogen ratio (C/N) and carbon/phosphorus ratio (C/P) of each raw compost shown in the raw compost formulation table in Table 2 were calculated based on the C/N ratios and C/P ratios of the sawdust, poultry manure and superphosphate used as raw materials, as well as, on the mixing ratio thereof The weight of the compost prepared to have a water content of 70% was 300 g/500 cc. Composting was continued at 60° C. for 33 days, and turning was carried out on the 21st day. Test results are shown in FIG. 4.

TABLE 3

| | Fermentation condition | | | Formulation | |
|---|---|---|---|---|---|
| Test No. | C/N | C/P | PCB addition form | Volume of raw material compost | PCB concentration |
| 1 | 15 | 30 | Cellulose | 500 cc | 1% |
| 2 | 15 | 30 | Glucose | 500 cc | 1% |
| 3 | 20 | 30 | Cellulose | 500 cc | 1% |
| 4 | 20 | 30 | Glucose | 500 cc | 1% |

Example 3
Biodegradation Test of Biodegradable Polymers

Difference in the biodegradability depending on the structure of biodegradable polymer was examined. Sea sand rinsed with distilled water, a compost and a polymer were taken into a 5-lilter plastic vessel according to the formulation shown in Table 5, and after the resulting mixture was stirred well, it was introduced to the reaction column 1 in the apparatus shown in FIG. 1 to measure the amount of carbonic acid gas formed under the following conditions:

quantity of air flow: 30 ml/min;

reaction temperature: 35° C.

Figure 5:
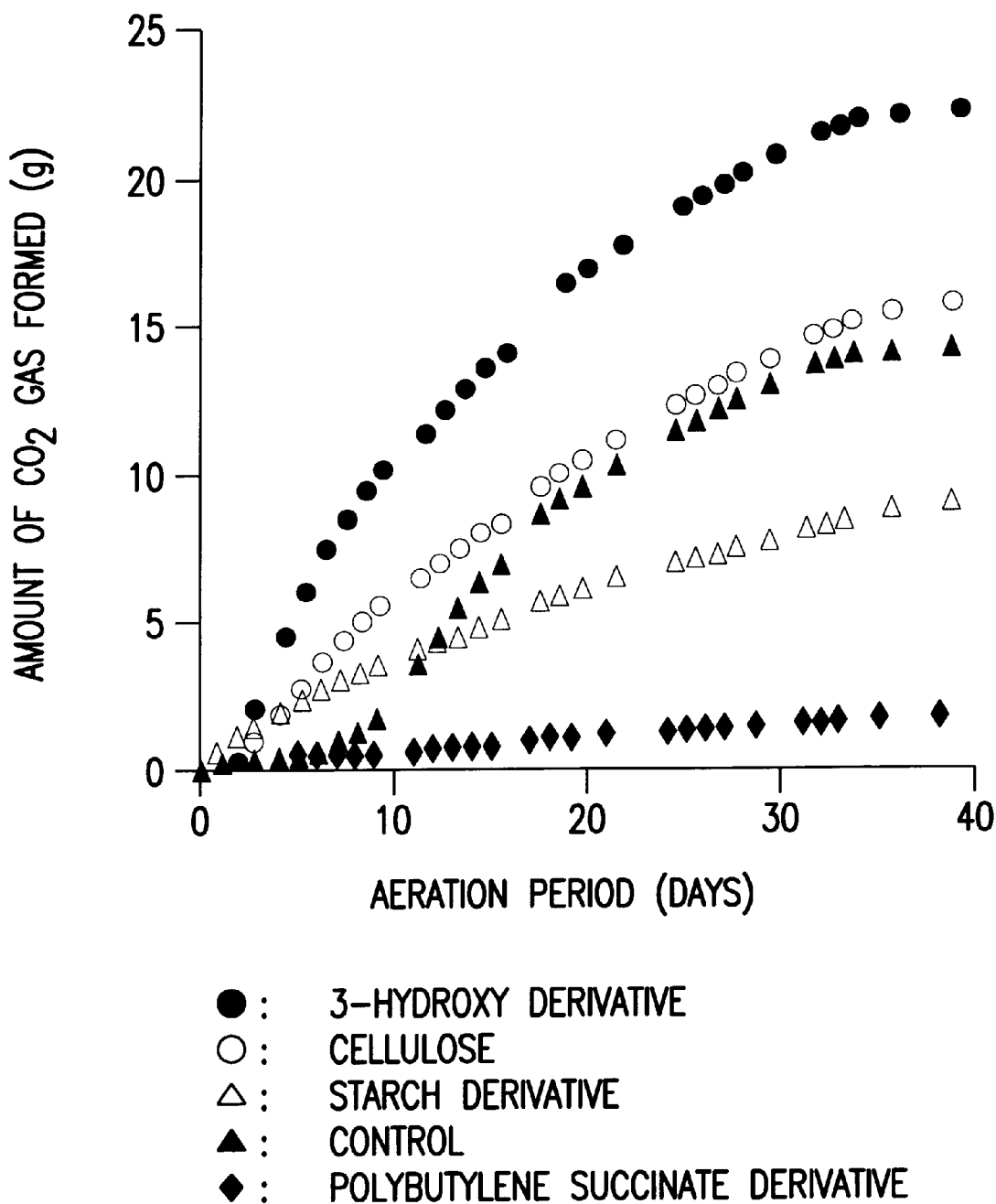
FIG. 5 is a view showing a measurement result of accumulated value of carbonic acid gas generated in Embodiment 3.

As the sea sand (grain size: 20 to 35 mesh), 250 ml of Wako's reagent grade sand was rinsed three times with distilled water, and the resulting sand from which the excess of water was decanted off was used. An aged farmyard compost made from sawdust and poultry manure was subjected to selection using a 6.5-mesh official sieve, and the 6.5-mesh under fractions were used as such. Each polymer was rinsed three times with distilled water, and the thus treated polymer from which the excess of water was decanted off was used. The results of measurement of accumulated amount of carbonic acid gas formed are shown in FIG. 5.

TABLE 5

| | | Mixing ratio | | |
|---|---|---|---|---|
| Sample No. | Polymer | Amount of polymer | Compost | Sea sand |
| 1 | 3-Hydroxybutyrate derivative | 10 g | 250 ml | 250 ml |
| 2 | Cellulose | 10 g | 250 ml | 250 ml |
| 3 | Polybutylene succinate derivative | 10 g | 250 ml | 250 ml |
| 4 | Starch derivative | 10 g | 250 ml | 250 ml |
| 5 | Control | 0 g | 250 ml | 250 ml |

Example 4
Application to an Organic Chlorine-containing Compound

Figure 6:
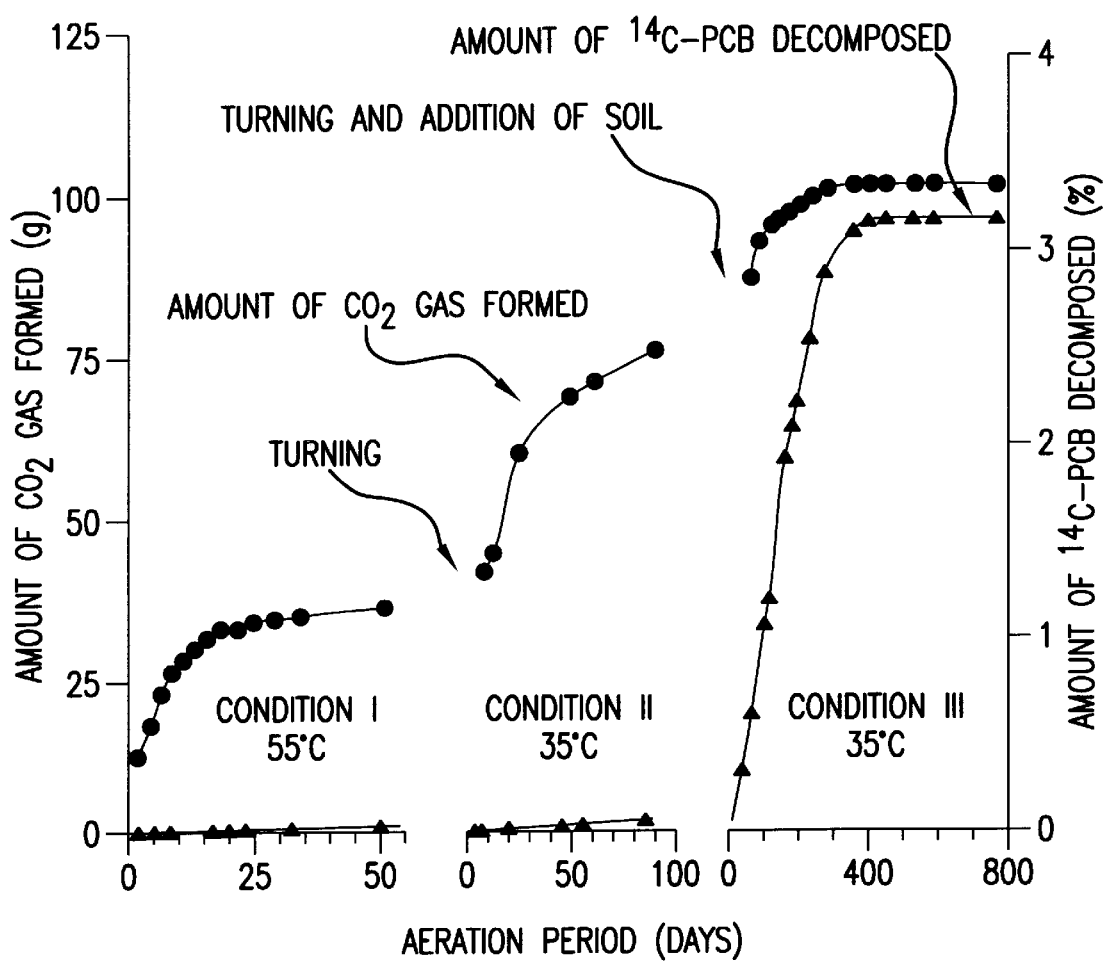
FIG. 6 is a view showing a measurement result of accumulated value of carbonic acid gas generated in Embodiment 4.

Degradability of the organic chlorine-containing compound PCB in the soil was measured using an isotope $^{14}C$—PCB. A compost raw material was prepared by mixing sawdust (136 g), poultry manure (22 g), superphosphate (1.45 g), water (76 g) and a $^{14}C$—PCB-coated cellulose (PCB/cellulose=10 mg/20 g) under stirring in a 5-liter stainless steel bowl. The thus prepared sample had a C/N ratio of 15, a C/P ratio of 30, a water content of 70% and a PCB concentration of 100 ppm. The sample was introduced into the reaction column 1 in the apparatus shown in FIG. 2, and the amount of carbonic acid gas formed and the amount of decomposed PCB were measured under the following three running conditions. The composting process was carried out stepwise in terms of a first fermentation step (55° C., 50 days), and a second fermentation step (35° C., 85 days) after turning. The former step and the latter step are referred to as the operation condition I and the operation condition II respectively. Further, a mixture of a soil (147 g of Mt. Fuji's Kuroboku soil) and the compost (83 g) having underwent the second fermentation step was prepared, and the apparatus was operated at 35° C. for 765 days (this step is Fuji's Kuroboku soil) and the compost (83 g) having underwent the second fermentation step was prepared, and the apparatus was operated at 35° C. for 765 days (this step is referred to as the operation condition III). Aeration was carried out in each case at a rate of 30 ml/min that is the aerobic fermentation condition. The amount of $^{14}C$—PCB decomposed into carbonic acid gas was determined by preparing a $^{14}C$—$BaCO_3$ powder from the $^{14}C$-carbonic acid gas captured in the 1N—NaOH solution, and the $^{14}C$—$BaCO_3$ powder thus prepared was quantitatively determined using a liquid scintillation counter. To a centrifuge tube (50 ml) were introduced the 1N—NaOH solution (20 ml), and then 4N—NaOH (5 ml) and 2N—$BaCl_2$ (20 ml) were added thereto, followed by separation of the supernatant over a centrifuge (4000 rpm×10 min). The precipitate of $^{14}C$—$BaCO_3$ thus formed was rinsed with distilled water (25 ml) and then centrifuged (4000 rpm, 5 min). After the $^{14}C$—$BaCO_3$ precipitate was rinsed by adding acetone (25 ml), it was centrifuged (4000 rpm×3 min), and the acetone was decanted off The residue was further rinsed twice with acetone in the same manner as described above. After the $^{14}C$—$BaCO_3$ thus formed was dried well in a desiccator under reduced pressure (1 mmHg), the weight of $^{14}C$—$BaCO_3$ was measured. The $^{14}C$—$BaCO_3$ formed (100 mg) and CAB—O—SIL (0.4 mg) were weighed using a counting vial, and after addition of a 0.3% (W/V) solution (10 ml) of PPO in toluene thereto, the resulting mixture was subjected to shaking, followed by measurement using a liquid scintillation counter to determine specific radioactivity of the $^{14}C$—$BaCO_3$ (100 mg). The total amount of carbonic acid gas formed was determined from the sum of the carbonic acid gas captured in the 1N—NaOH solution and that captured in the adsorption column. The amount of carbonic acid gas formed and the amount of decomposed PCB are indicated to be standardized in terms of the amount of gas formed per 100 g (dry weight) of the compost. That is, the accumulated value of the carbonic acid gas formed and that of the PCB decomposed are shown in FIG. 6.

What is claimed is:

1. A method for evaluating microbial-degradability of an organic matter, the method comprising the steps of:

placing an organic matter as an evaluation subject together with a prescribed microbial source into a reaction column maintained constantly at a fixed temperature to effect decomposition of the organic matter in the reaction column by microorganisms contained in the prescribed microbial source under feeding of $CO_2$-free saturated water vapor into the reaction column and to measure the weight of carbon dioxide formed by the decomposition;

placing a cellulose as a evaluation reference together with the same prescribed microbial source as described above into another reaction column maintained constantly at the same fixed temperature as described above to effect decomposition of the cellulose in the reaction column by the microorganisms contained in the prescribed microbial source under feeding of $CO_2$-free saturated water vapor into the reaction column and to measure the weight of carbon dioxide formed by the decomposition; and carrying out comparative discussion of these two measured values so as to evaluate degradability of the organic matter.

2. The method according to claim 1, wherein a mixture of a compost having a predetermined formulation and sea sand is used as the prescribed microbial source.

3. The method according to claim 1, wherein the weight of carbon dioxide formed by the decomposition of the organic matter and the weight of carbon dioxide formed by the decomposition of the cellulose are determined by allowing each carbon dioxide to be adsorbed by soda lime and measuring the weight gain in the soda lime.

4. The method according to claim 2, wherein the weight of carbon dioxide formed by the decomposition of the organic matter and the weight of carbon dioxide formed by the decomposition of the cellulose are determined by allowing each carbon dioxide to be adsorbed by soda lime and measuring the weight gain in the soda lime.

5. An apparatus for evaluating microbial-degradability of an organic matter, the apparatus comprising:

a reaction column maintained constantly at a fixed temperature and containing an organic matter as an evaluation subject or a cellulose as an evaluation reference together with a prescribed microbial source;

means for forming saturated water vapor, connected to one end of the reaction column, the means being provided with first $CO_2$ adsorption means and feeding $CO_2$-free saturated water vapor into the reaction column; and an adsorption column, connected to the other end of the reaction column, the adsorption column containing second carbon dioxide adsorption means.

6. The apparatus according to claim 5, wherein a mixture of a compost having a predetermined formulation and sea sand is used as the prescribed microbial source.

7. The apparatus according to claim 5, wherein the first and second carbon dioxide adsorption means each are soda lime.

8. The apparatus according to claim 6, wherein the first and second carbon dioxide adsorption means each are soda lime.

9. The apparatus according to claim 5, wherein the adsorption column is connected to the other end of the reaction column via a water-removing column or a desiccation column.

10. The apparatus according to claim 6, wherein the adsorption column is connected to the other end of the reaction column via a water-removing column or a desiccation column.

11. The apparatus according to claim 7, wherein the adsorption column is connected to the other end of the reaction column via a water-removing column or a desiccation column.

12. The apparatus according to claim 8, wherein the adsorption column is connected to the other end of the reaction column via a water-removing column or a desiccation column.

* * * * *